(12) United States Patent
Bosma et al.

(10) Patent No.: US 8,088,133 B2
(45) Date of Patent: Jan. 3, 2012

(54) TONGUE CLEANING DEVICE

(75) Inventors: Mary Lynn Bosma, Weybridge (GB); Helen Chrisp, Weybridge (GB); Martin Kay, London (GB); Stephen Sayers, London (GB)

(73) Assignee: Glaxo Group Limited, Middlesex (GB)

( * ) Notice: Subject to any disclaimer, the term of this patent is extended or adjusted under 35 U.S.C. 154(b) by 81 days.

(21) Appl. No.: 11/912,426

(22) PCT Filed: Apr. 21, 2005

(86) PCT No.: PCT/EP2006/003868
§ 371 (c)(1),
(2), (4) Date: Oct. 24, 2007

(87) PCT Pub. No.: WO2006/114296
PCT Pub. Date: Nov. 2, 2006

(65) Prior Publication Data
US 2008/0154291 A1    Jun. 26, 2008

(30) Foreign Application Priority Data

Apr. 25, 2005 (GB) .................................. 0508374.6
Jul. 22, 2005 (GB) .................................. 0515164.2
Feb. 24, 2006 (GB) .................................. 0603777.4

(51) Int. Cl.
*A61B 17/24* (2006.01)
(52) U.S. Cl. ........................................ 606/161
(58) Field of Classification Search ............... 132/322; 433/80, 88–90, 141, 144; 601/162, 165; 606/161
See application file for complete search history.

(56) References Cited

U.S. PATENT DOCUMENTS

| | | | |
|---|---|---|---|
| 1,658,706 A | | 2/1928 | Carrott |
| 2,218,072 A | | 10/1940 | Runnels |
| 4,024,874 A | * | 5/1977 | Klippel .................... 606/106 |
| 5,005,246 A | * | 4/1991 | Yen-Hui ..................... 15/111 |
| 5,193,672 A | * | 3/1993 | Long .......................... 206/45.2 |
| 5,779,654 A | | 7/1998 | Foley et al. |
| 5,984,935 A | * | 11/1999 | Welt et al. ................... 606/161 |
| 6,089,865 A | | 7/2000 | Edgar |
| 6,132,445 A | | 10/2000 | Pavanelli et al. |
| 6,139,558 A | | 10/2000 | Wagner |
| 6,647,581 B1 | * | 11/2003 | Persad et al. ................ 15/111 |
| 2002/0128673 A1 | | 9/2002 | Ripich et al. |
| 2003/0191417 A1 | * | 10/2003 | Welt et al. ................... 601/134 |
| 2005/0048438 A1 | | 3/2005 | Gwen |
| 2005/0069372 A1 | * | 3/2005 | Hohlbein et al. ............ 401/132 |

FOREIGN PATENT DOCUMENTS

CA  2 254 550  5/2000

(Continued)

*Primary Examiner* — Ryan Severson
*Assistant Examiner* — Ashley Cronin
(74) *Attorney, Agent, or Firm* — Joshua C. Sanders; Nora L. Stein; Theodore R. Furman

(57) ABSTRACT

A tongue cleaning device comprising a tongue cleaning surface supported for tongue cleaning by running the surface across the tongue, a reservoir for a tongue cleaning fluid, means to dispense the fluid either onto the tongue cleaning surface, or directly onto the user's tongue, with a cover part, the tongue cleaning surface and cover part being relatively moveable between a position in which the tongue cleaning surface is exposed for use and a position in which the tongue cleaning surface is covered by the cover part.

14 Claims, 7 Drawing Sheets

FOREIGN PATENT DOCUMENTS

| | | |
|---|---|---|
| EP | 1 034 721 | 9/2000 |
| GB | 2 265 831 | 10/1993 |
| WO | WO 98/08458 | 3/1998 |
| WO | WO 00/01311 | 1/2000 |
| WO | WO 01/41659 | 6/2001 |
| WO | WO 01/45573 | 6/2001 |

* cited by examiner

Fig. 17.
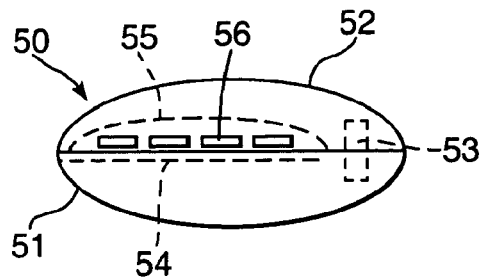
Fig. 18.
Fig. 18A.
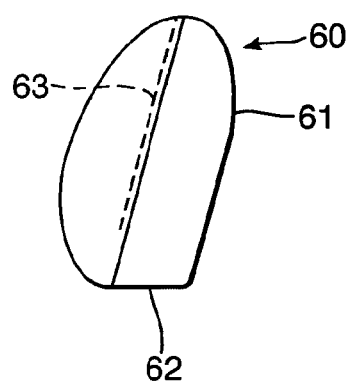
Fig. 18B.
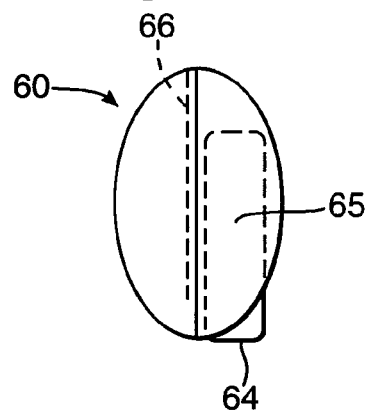
Fig. 18C.
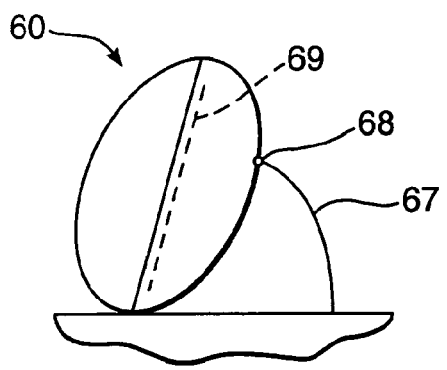
Fig. 18D.
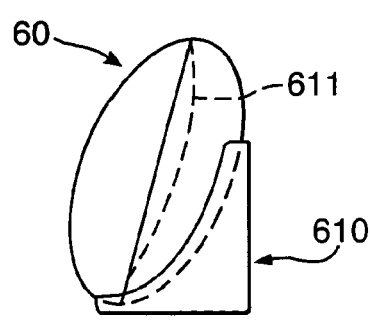

Fig.19.
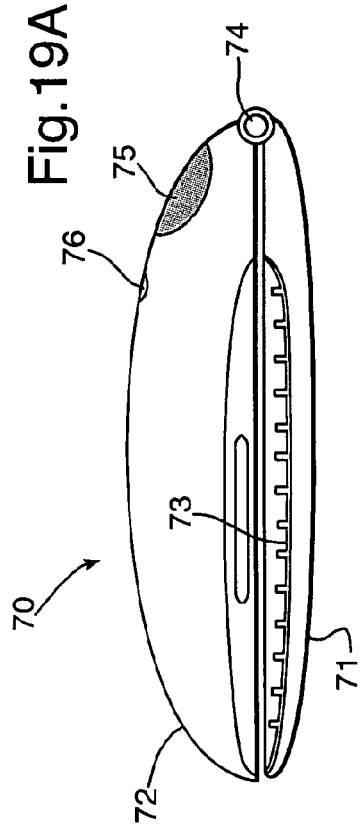
Fig.19A.
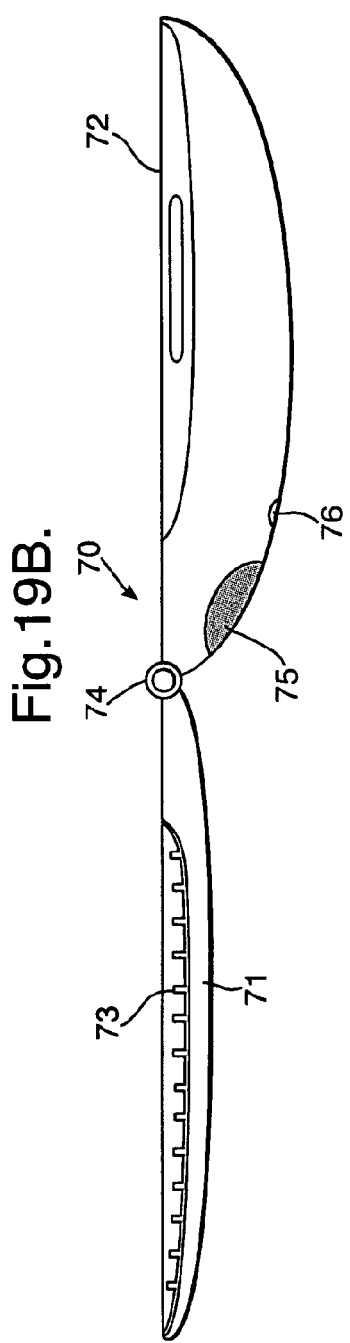
Fig.19B.
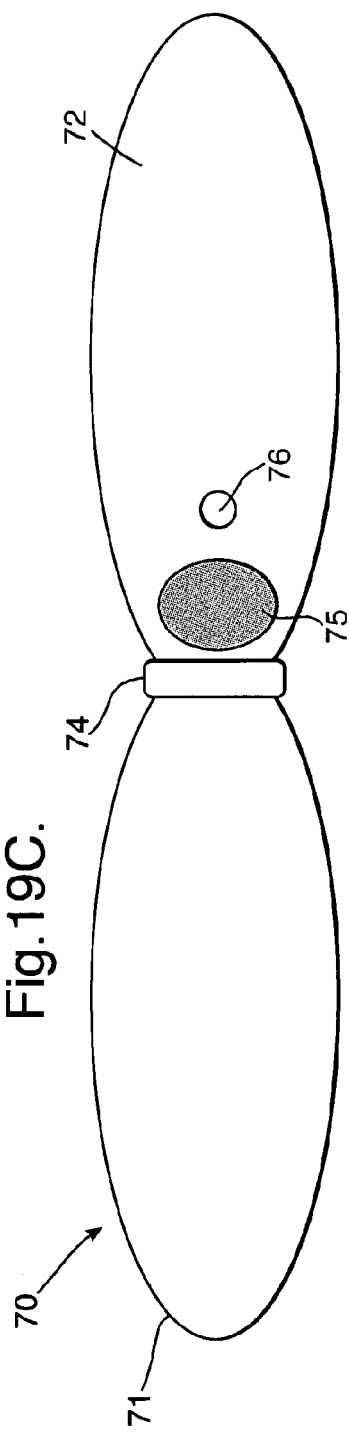
Fig.19C.

Fig. 20.
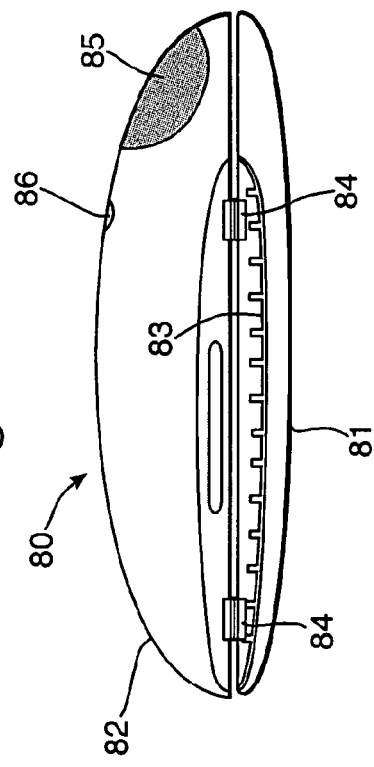
Fig. 20A.
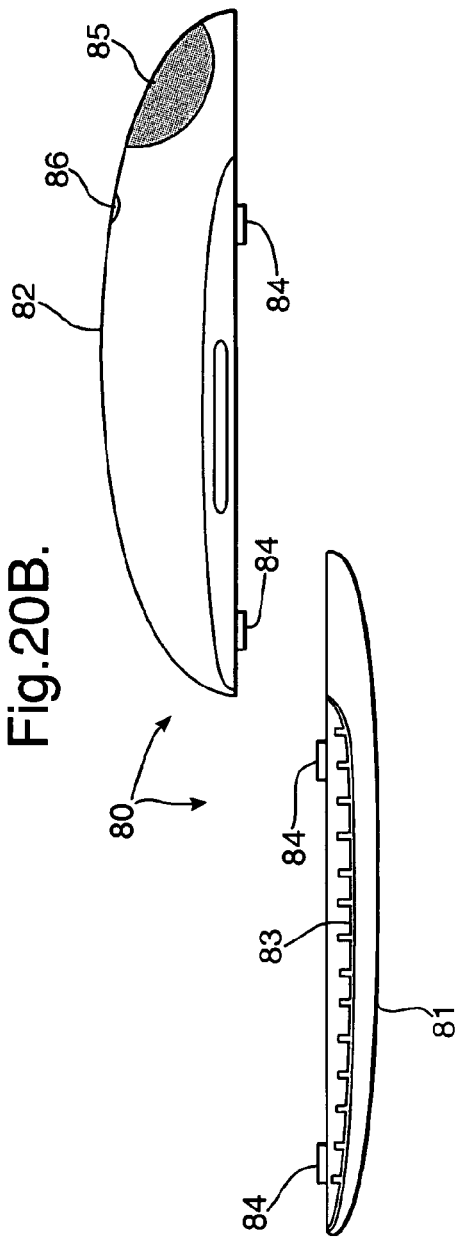
Fig. 20B.

TONGUE CLEANING DEVICE

This application is a §371 national phase entry of International Application No. PCT/EP06/03868, filed Apr. 25, 2005.

This invention relates to devices for tongue cleaning.

Cleaning of the tongue is considered desirable for the purpose of removing deposits from the tongue which might harbour bacteria and could consequently lead to bad breath or other oral health problems.

Devices for cleaning the tongue are known, generally comprising a surface to be moved across and in contact with the user's tongue, bearing projections, e.g. hemispherical or conical projections, or elongate ridges. Generally such a device is used for tongue cleaning by running the surface reciprocally across the tongue. For example in the case of projections which are ridges, the ridges may be moved reciprocally in a direction transverse to the elongate direction of the ridges. The device may be made of various materials provided these are safe for use in the oral cavity, such as plastics material e.g. polypropylene, or elastomeric projections. Various devices for cleaning the tongue are known in the art. For example U.S. Pat. No. 6,132,445 discloses a device which has a head which can be made of a semi-stiff material such as a rubbery material, with protuberances on its surface for tongue cleaning, and with openings in this surface via which a tongue cleaning fluid may be ejected through holes in the surface. The device of U.S. Pat. No. 6,132,445 includes a reservoir for the fluid from which the fluid may be pumped via a conduit toward the openings. Tongue cleaning devices with a facility for dispensing tongue cleaning fluid onto the tongue are also disclosed in U.S. Pat. No. 6,139,558, WO-A-00/01311, WO-A-01/41659, U.S. Pat. No. 5,779,654 and U.S. Pat. No. 6,089,865. The devices disclosed therein are generally elongate toothbrush-like devices and it is an object of this invention to provide a more convenient construction of device.

According to a first aspect of this invention a device for tongue cleaning is provided comprising;

a tongue cleaning surface which is supported for tongue cleaning by running the surface across and in contact with the tongue in a tongue cleaning direction, a reservoir for a tongue cleaning fluid, means to dispense said fluid either (a) onto the tongue cleaning surface, or (b) directly onto the user's tongue, a cover part, and wherein the tongue cleaning surface and cover part are relatively moveable between a first position in which the tongue cleaning surface is exposed for use and a second position in which the tongue cleaning surface is covered by the cover part.

By means of the device the fluid may be dispensed onto the tongue cleaning surface, either directly or indirectly via the user's tongue.

Suitably the tongue cleaning surface is a surface of an elastomeric, i.e. rubbery, member having said tongue cleaning surface. Preferably there are projections, e.g. integral projections, from the tongue cleaning surface to facilitate tongue cleaning e.g. by increasing the abrasive effect between the tongue cleaning surface and the tongue. The projections may for example be conical, hemispherical, or in the form of ridges across the whole or part of the tongue cleaning surface.

Suitably the tongue cleaning surface may comprise at least one ridge with its ridge length direction arranged transverse to the tongue cleaning direction, its ridge thickness in the tongue cleaning direction, and its ridge height perpendicular to the tongue cleaning direction.

The tongue cleaning surface may comprise a member defining a concavity having a bottom surface and bounded by an upper rim and having a depth direction perpendicular to the tongue cleaning direction, and supported within the concavity at least one ridge having a ridge length direction transverse to the tongue cleaning direction, wherein the at least one ridge has a profile in the ridge length direction which rises away from the bottom surface in a convex curved shape.

The tongue cleaning surface has an end in the tongue cleaning direction which in use in tongue cleaning first enters the user's mouth, termed herein the "forwards", and an opposite end termed herein the "rear end". The rear end toward front end direction is herein termed "forwards", and the opposite direction is termed herein "backwards". The movement of the tongue cleaning surface in the direction into the user's mouth is termed herein the "in stroke", and the movement of the tongue cleaning surface in the direction out of the user's mouth is termed herein the "out stroke"

Suitably the concavity is of an oval shape in plan as seen looking downwards towards the bottom surface with its major axis aligned with the tongue cleaning direction, so that the concavity is a partial ellipsoid in shape.

Suitably such an at least one ridge has a profile which rises to a curved convex peak with its highest point adjacent the transverse mid point of the concavity. Suitably such that at least one ridge has a profile which comprises a curved convex peak with a curved concave dip on either lateral side of the peak. Suitably the height to which the curved convex shape of the profile of the ridge rises above the bottom surface of the concavity is less than the depth of the concavity in the vicinity of the ridge. This has the consequence that the edge of the ridge remote from the bottom surface lies below the rim of the concavity. It is found that the tongue cleaning surface of this second aspect of the invention, comprised of such ridges facilitates better contact of the ridges to the surface of the user's tongue, particularly to the central ridge of the user's tongue.

In its ridge length direction the at least one ridge may in shape be a straight line, or may be gently curved, for example in an arc which is convex in the direction in which the member is to be inserted into the user's mouth.

There may be plural ridges, and if present these are preferably arranged sequentially in the tongue cleaning direction. The edges of plural ridges may all lie in a straight line as sectioned along the tongue cleaning direction, but preferably such edges lie in a convex or concave curve such that in use the ends in such convex or concave curve contact the user's tongue. The edges of plural ridges may lie in a line which as sectioned along the tongue cleaning direction from the forward end toward the rear end descends in the height direction of the ridges.

When there are plural ridges arranged sequentially in the tongue cleaning direction then the ridges may all have the same flexibility characteristics under the forces experienced during tongue cleaning. Alternatively, and preferably, less flexible ridges may be concentrated nearer to or adjacent the forward end e.g. to facilitate outward drag of surface coatings on the tongue toward the front of the tongue during the out stroke, and more flexible ridges may be concentrated nearer to or adjacent the rear end e.g. to massage the tongue. For example less flexible ridges may have a greater thickness in the tongue cleaning direction than more flexible ridges, or less flexible ridges may have a lesser height:maximum thickness ratio relative to the more flexible ridges.

A ridge may have a cross section when cut along the tongue cleaning direction which is symmetrical. Preferably a ridge has an asymmetrical section as cut along this direction, in that the end radius of the ridge adjacent to the direction in the tongue cleaning direction in which the ridge is to be inserted into the user's mouth is greater than the end radius of the ridge adjacent to the direction in the tongue cleaning direction in which the ridge is to be removed from the user's mouth. Such a section can help the ridge to glide more comfortably along the tongue on insertion into the user's mouth, with at the same time effective scraping of deposits from the user's tongue toward the open mouth during the removal action.

One or more ridge may be combined in the tongue cleaning surface with other types of tongue cleaning means, such as part—e.g. hemi-spherical or ovoid domed or conical integral projections from the tongue cleaning surface.

Suitably the one or more ridge is made of an elastomeric material, and is integrally made with an elastomeric member, for example such a member may comprise part of the bottom surface of the concavity.

The elastomeric member may for example be supported by a backing, e.g. of a rigid plastic material, and/or by a frame e.g. of plastic material, wholly or partly surrounding the member and e.g. supporting the member at its perimeter.

One form of such a backing, particularly suitable for the second aspect of the invention, may comprise a part in the form of a shell, e.g. made of a plastics material, defining the bottom surface of a cavity, with one or more support extending upward into the cavity, the one or more support supporting the elastomeric member. For example such support may comprise one or more rib. Suitably there are plural supports e.g. plural ribs. For example plural ribs may be made integrally with such a plastics material shell and may extend in a rib length direction across the longitudinal direction, and the elastomeric member may be supported on the tongue cleaning surface defined by the upper edges of such plural ribs. Such an arrangement provides a light but robust construction and can minimise the quantity of plastics material required for the device of the invention.

Certain features of the tongue-cleaning surface of the device of this invention appear to be novel and inventive, and beneficial for tongue cleaning devices generally.

Consequently in a second aspect, this invention provides a device for tongue cleaning comprising a tongue cleaning surface which is supported for tongue cleaning by running the surface across and in contact with the tongue in a tongue cleaning direction, wherein the tongue cleaning surface comprises a member defining a concavity having a bottom surface and bounded by an upper rim and having a depth direction perpendicular to the tongue cleaning direction, and supported within the concavity at least one ridge having a ridge length direction transverse to the tongue cleaning direction, wherein the at least one ridge has a profile in the ridge length direction which rises away from the bottom surface in a convex curved shape.

Preferred features of such a concavity, e.g. its shape, of a ridge e.g. its materials, profile, cross section, and shape, arrangement of plural ridges, support etc. may be as described above with respect to the first aspect of this invention.

The means to dispense the fluid onto respectively the tongue cleaning surface or the user's tongue may include pump means to pump the fluid from the reservoir to a dispensing orifice from which the fluid may be dispensed. There may be a conduit providing communication between the pump means and the orifice.

Known types of pump means may be used. Suitable small pumps are commercially available, e.g. based on those used for perfume sample spray bottles, typically being cylindrical with a diameter ca. 13 mm, and e.g. from the company Rexam. For example the reservoir may be flexible and compressible so that it may be compressed by the user's hand pressure to thereby pump fluid out of the reservoir. For example the reservoir may be pressurised by a compressed gas to drive fluid content out of the reservoir. For example there may be a pump between the reservoir and a dispensing orifice. There may be a one-way valve between the reservoir and the orifice(s) biased to allow fluid flow from the reservoir toward the orifice(s). The reservoir may be replaceable. The tongue cleaning fluid may be a tongue cleaning fluid gel.

Typically the device may dispense ca. 0.75 ml of fluid at a time, and the reservoir may have a capacity ca. 22.5 ml, e.g. one months supply if used once a day.

In option (a) the means to dispense a fluid onto the said tongue cleaning surface may comprise one or more orifice in the tongue cleaning surface, for example passing completely through the tongue cleaning surface, e.g. a tongue cleaning surface in the form of a diaphragm. For example in option (a) the fluid may be dispensed onto the tongue cleaning surface before the tongue cleaning surface is applied to the tongue, or whilst the tongue cleaning surface is applied to the tongue.

In option (b) the means to dispense a fluid onto the user's tongue may comprise a dispensing orifice, e.g. a nozzle such as a spray nozzle on the device, positioned so that fluid may be dispensed therefrom onto the user's tongue, before the tongue cleaning surface is applied to the user's tongue.

The tongue cleaning surface, and preferably the support if present, is moveable between a first position in which the tongue cleaning surface is exposed for use and a second position in which the tongue cleaning surface is covered by the cover part. This may be achieved in various ways. In one construction the device is constructed in two parts being a first part comprising the tongue cleaning surface, and a second part comprising the cover part, and the first and second parts may be relatively moveable so that in the second position the cover part covers the tongue cleaning surface. The cover part may comprise an area of such a second part which in the second position is adjacent to the tongue cleaning surface. For example the tongue cleaning surface and the cover part may both comprise surfaces which in the second position are in a facing relationship with each other and in close proximity.

Such a second part may incorporate a reservoir of the tongue cleaning fluid.

For example such first and second parts may be relatively slideably movable relative to each other so that in the second position the second part covers the tongue cleaning surface. For example the first and second parts may have co-operating guide means to retain the first and second parts together and to guide them in this sliding movement.

In a preferred construction the first and second parts may be pivotally movable relative to each other so that in the second position the cover part covers the tongue cleaning surface. For example the first and second parts may be connected by a pivotal connector that allows such pivoting movement. Suitably the first and second parts may have corresponding oval shapes, particularly if the tongue cleaning surface comprises the oval concavity of the second aspect of the invention, and the pivotal connector may be located near to one of the ends of the long axis of the oval shape. The second part may comprise a cover part which when the first part is in the second position covers the tongue cleaning surface, and the pivotal connector may be positioned relative to the first and second parts that in the second position the cover part covers the tongue cleaning surface. In a preferred construction the relative pivoting motion may be in a plane substantially parallel to the tongue cleaning surface, i.e. about a pivot axis perpendicular to this plane. In another construction in which the first and second parts are relatively pivotally moveable the first and second parts may be pivotally hinged in a so called "clamshell" configuration, now familiar with e.g. mobile telephones. In such a configuration the first part including the tongue cleaning surface and the second part are hinged adjacent their respective perimeters, and the second part is able to swing through an obtuse angle, e.g. ca. 180° in a swing plane perpendicular to the plane of the tongue cleaning surface, about a pivot axis parallel to the plane of the tongue cleaning surface. By "plane of the tongue cleaning surface" is not implied that this surface is planar, but that it can be generally represented by a "best fit" constructed plane.

For example the first and second parts may be relatively moveable to the extent that they are completely separable from each other to thereby expose the tongue cleaning surface. For example the two parts may be releasably connected together by means of a snap-fit or friction fit connections, of a conventional type, or some convenient latch.

In one embodiment suitable for option (a), to dispense the fluid onto the tongue cleaning surface the above-mentioned conduit may pass through a connector between such first and second parts, for example through a pivotal connector between the first and second parts, and such a conduit may communicate with a conduit located on the opposite side of the tongue cleaning surface to convey the fluid from the conduit toward one or more dispensing orifice in the tongue cleaning surface.

In one embodiment suitable for option (b), to dispense the fluid onto the tongue cleaning surface the second part may incorporate a reservoir for the fluid, a means to dispense the fluid from the reservoir, and an orifice in the second part from which the fluid may be dispensed onto the user's tongue.

In another embodiment suitable for option (b), to dispense the fluid onto the tongue cleaning surface the second part may incorporate a reservoir for the fluid, a means to dispense the fluid from the reservoir, a conduit to convey the fluid to the first part, and an orifice in the first part from which the fluid may be dispensed onto the user's tongue. Such a conduit may pass through a connector between the first and second parts, for example through a pivotal connector between the first and second parts, and such a conduit may communicate with a further conduit located on the opposite side of the tongue cleaning surface to convey the fluid toward the orifice in the first part.

Further features of the device may be provided to enhance the effectiveness of the device, especially the hygiene of the device.

For example the device may be provided with means to facilitate the access of air to the tongue cleaning surface when the cover part is in its second position covering the tongue cleaning surface. Access of air can help to prevent bacterial growth and can oxidise contaminants on the tongue cleaning surface. For example the device may have one or more aperture therein providing communication of air between the outside of the device and the tongue cleaning surface. In a two-part device as described above such one or more aperture may be in the second part.

For example the device may be of a shape or construction which facilitates the device being placed in a rest position in which the tongue cleaning surface is aligned with a vertical component, e.g. at an angle of 45° or more to the horizontal so that residual liquid on the tongue cleaning surface will tend to run off. For example the device may be shaped with a base upon which it may be stood such that the tongue cleaning surface is aligned in such an orientation. For example such a base may be provided by the profile of the outer surface of the above-mentioned first or second part of the device. For example such a base may be provided by the outer surface of a reservoir incorporated into the device and projecting beyond the envelope of the device. For example the device may be provided with a support which may support it with the tongue cleaning surface in such an alignment, for example an extendible or hinged support which may be extended or hinged out from the outer surface of the device to thereby provide a leg for the device to lean upon. For example the device may be provided together with a cradle in which it may rest and which supports the device with the tongue cleaning surface in such an alignment.

In use the device may be moved into its first position so the tongue cleaning surface is exposed for use, the fluid may be applied to the tongue cleaning surface, and the tongue cleaning surface may be used to clean the tongue, e.g. removing tongue deposits, by for example a reciprocal movement of the tongue cleaning surface across the tongue in the tongue cleaning direction. The device may then be cleaned after use, e.g. by rinsing it in water or a cleansing liquid. Preferably after use and such cleaning the device is placed in a rest position in which the tongue cleaning surface is aligned with a vertical component, e.g. at an angle of 45° or more so that residual liquid on the tongue cleaning surface will tend to run off, for example by the means described above.

Suitable tongue-cleaning fluids include known commercially available mouthwash formulations, which may be alcohol-free or contain alcohol, and may contain an antibacterially active material such as hydrogen peroxide (in an amount complying with local regulations, e.g. in the EU ca. 0.1%) or cetylpyridinium chloride (typically 0.07%), and may be flavoured e.g. mint. Suitable such formulations are commercially available e.g. as OASIS™ sold under the Sensodyne™ brand by GlaxoSmithKline, PRO-HEALTH™ sold under the Crest™ brand by Procter & Gamble, and FLUORIGUARD™ sold by Colgate-Palmolive.

The invention will now be illustrated by way of example only with reference to the accompanying drawings.

FIG. 17 shows a device of this invention with openings to provide access of air to the tongue cleaning surface.

FIG. 18 shows means by which a device of this invention may be placed in a rest position with the tongue cleaning surface inclined.

FIG. 19 shows views of another device of this invention.

FIG. 20 shows views of another device of this invention.

Figure 1:
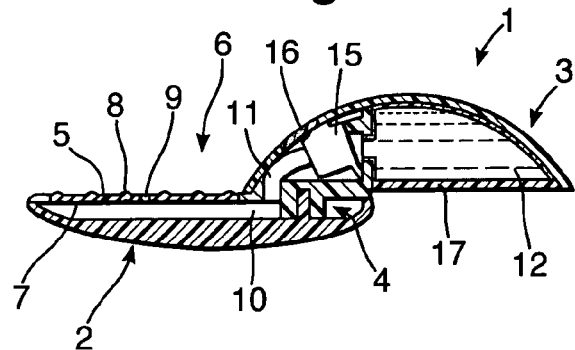
FIG. 1 shows a sectional view of a device of the invention in its first position.

Referring to FIGS. 1 to 4 a device for tongue cleaning according to option (a) is shown overall 1. This device 1 comprises a first part 2 and a second part 3 pivotally connected at 4. The first part 2 is made of plastics material and is generally in the form of a hemi-ellipsoidal shell.

Mounted across the elliptical opening of the first part 2 is an elastomeric member 5 in the form of a thin layer of elastomeric material which has a tongue cleaning surface 6 and which is supported by means of a rigid plastics material (e.g. polypropylene) backing member 7. There are plural integral hemispherical projections 8 from the tongue cleaning surface 6. Apart from the projections the tongue cleaning surface 6 is generally flat. The support 7 snap-fits into a suitable snap-fit connection at the shell rim of first part 2. There is an orifice 9 in tongue cleaning surface 6 passing completely through the member 5 and the backing member 7, and communicating with a conduit 10 within first part 2. Conduit 10 is in communication with a further conduit 11 passing through the pivotal connection 4 and providing communication between first part 2 and second part 3.

The second part 3 is also generally in the form of a plastics material shell. Part 3 houses a complementary fitting reservoir 12 for a tongue cleaning fluid. Reservoir 12 has an outlet nozzle 13 for the fluid it contains and which connects with a connector 14 in part 3.

Second part 3 also incorporates a mechanical pump means 15 which can pump fluid from the reservoir 12 when this is connected to part 3 through conduits 11 and 10 to orifice 9. Pump 15 is of known type such as a piston pump, and is operable by a user's hand pressure deforming a flexible diaphragm 16 in part of the shell of part 3 toward and into contact with pump 15. There may be a one-way valve (not shown) between reservoir 12 and the orifice 9 biased to allow fluid flow from reservoir 12 toward orifice 9.

Figure 5:
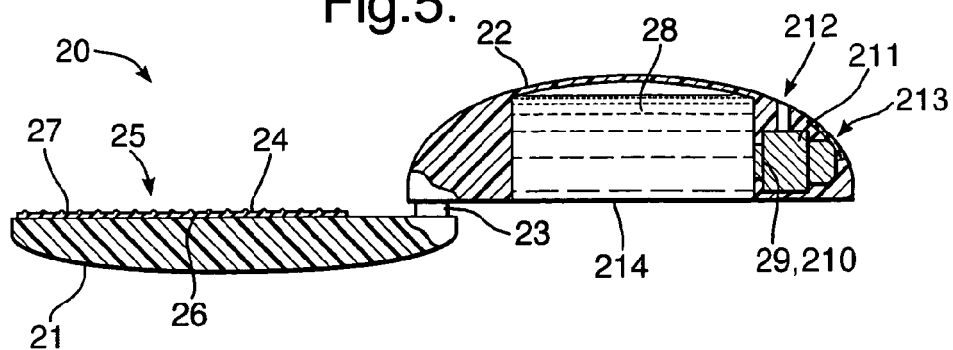
FIG. 5 shows a sectional view of another device of the invention in its first position.
Figure 6:
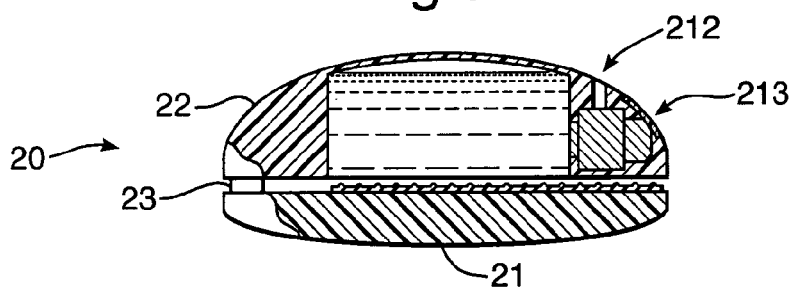
FIG. 6 shows a sectional view of the device of FIG. 5 in its second position.
Figure 7:
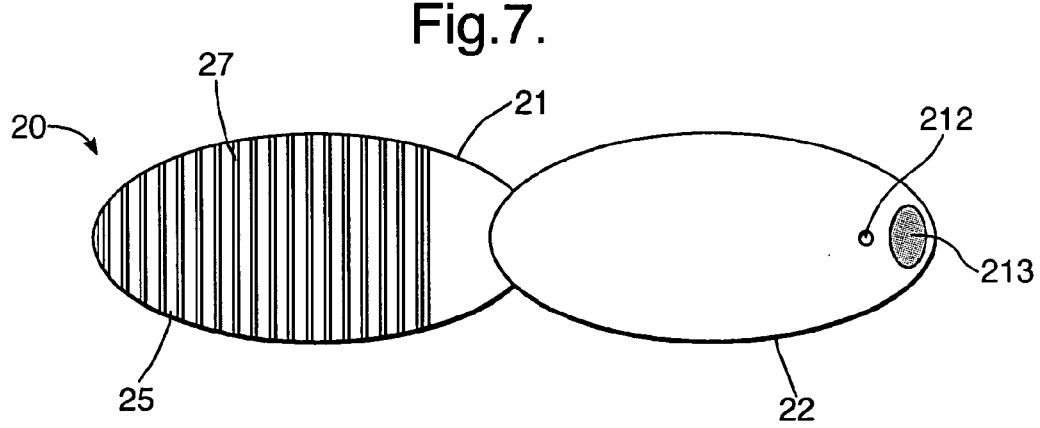
FIG. 7 shows a plan view of the device of FIG. 5 in its first position.

Referring to FIGS. 5, 6 and 7, a device 20 according to option (b) of the invention is shown. It is seen that the overall shape and layout of the device 20 is similar to that of the device of FIGS. 1 to 4. The device 20 comprises a first part 21 and a second part 22, pivotally connected at 23. The parts 21 and 22 are again both in the form of semi-ellipsoidal shells. Mounted across the elliptical opening of the shell of part 21 is an elastomeric member 24 in the form of a thin layer of elastomeric material which has a tongue cleaning surface 25 which is supported by means of a rigid plastics material backing member 26. The surface 25 of the elastomeric member 24 is ribbed 27.

Second part 22 houses a complementary fitting reservoir 28 for a tongue cleaning fluid. Reservoir 28 has an outlet nozzle 29 for the fluid it contains and which connects with a connector 210 in part 22. Second part 22 also includes a pump means 211 which can pump fluid from reservoir 28 to an orifice 212 being an outlet spray nozzle. Pump 211 is also of known type and is operable by a user's hand pressure deforming a flexible diaphragm 213 in part of the shell of part 22 toward and into contact with pump 211. There may be a one way valve between reservoir 28 and orifice 212 biased to allow fluid to flow from reservoir 28 toward orifice 212.

In FIGS. 1, 3, 4, 5, and 7 the device 1 is shown in its first position in which the tongue cleaning surface 6 is exposed for use.

Figure 2:
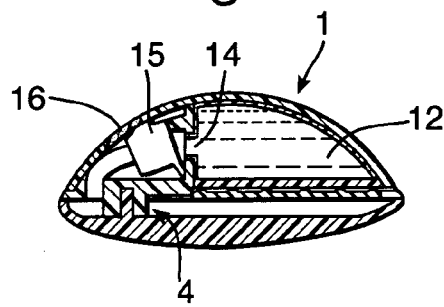
FIG. 2 shows a sectional view of a device of the invention in its second position.
Figure 3:
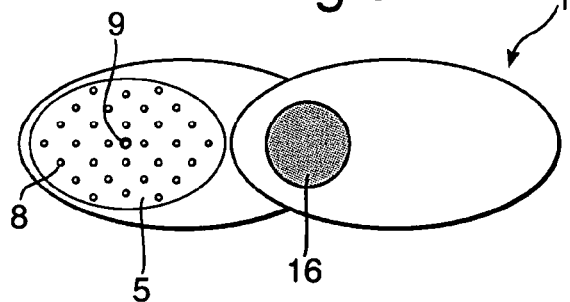
FIG. 3 shows a plan view of a device of the invention in its first position.
Figure 4:
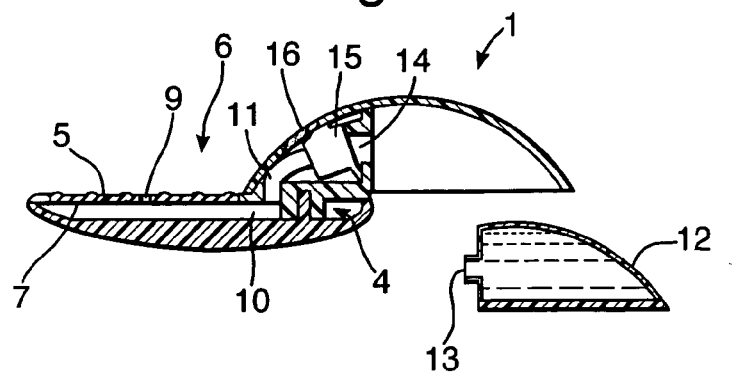
FIG. 4 shows a sectional view of a device of the invention in its first position, with the reservoir removed.

In FIGS. 2 and 6 the device 1 is shown in its first position in which the tongue cleaning surface 6 is covered. This is achieved by the pivotal movement relative to each other of the first and second parts 2, 3, 21, 22 about the pivotal connection 4, 23. It is seen that the first and second parts 2, 3, 21, 22 are of semi-ellipsoidal shape with a similar elliptical plan shape as seen in FIGS. 3 and 7. The pivotal connection 4, 23 is located on the long axis of the elliptical shape close to the perimeter of the elliptical shape so that in the first position the tongue cleaning surface 6, 25 is swung out from under the second part 3, 22 and in the second position the tongue cleaning surface 6 is swung back under the second part 3, about a pivot axis extending perpendicular to the plane of these elliptical shapes. Second part 3, 22 has a cover part 17, 214 being a surface of reservoir 12, 28 which when the first part 2 is in the second position covers the tongue cleaning surface 6.

In use the device 1 of FIGS. 1-4 is normally kept in its second position as seen in FIG. 2 so that tongue cleaning surface 6 is covered by cover part 17 and consequently protected from contamination, damage or leakage of fluid through the orifice 9. For use the device is moved into its first position as seen in FIGS. 1 and 3 so the tongue cleaning surface 6 is exposed for use. The pump 15 is operated to apply a suitable volume of fluid to the tongue cleaning surface. For example one stroke of the pump 15 may dispense ca. 0.75 ml of fluid through orifice 9. The tongue cleaning surface 5 may then be moved reciprocally across the user's tongue to clean the tongue, e.g. removing tongue deposits.

In use the device 20 of FIGS. 5-7 is normally kept in its second position as seen in FIG. 6 with the tongue cleaning surface 25 covered by cover part 214. For use, firstly the device is positioned so that the orifice 212 is aimed at the user's tongue, and the pump 211 is operated to spray the fluid in reservoir 28 onto the user's tongue. This may be done with the device 20 in either the first or second positions. Then with the device 20 in its first position as shown in FIG. 5 or 7 the tongue cleaning surface 25 is applied to the tongue and the ribs 27 moved reciprocally across the tongue surface to clean the tongue.

After the device 1, 20 has been used in this manner the tongue cleaning surface 6, 25 may be cleaned, e.g. rinsed under a water tap, and the device 1, 20 returned to the second position as seen in FIG. 2 or 6.

Figure 8:
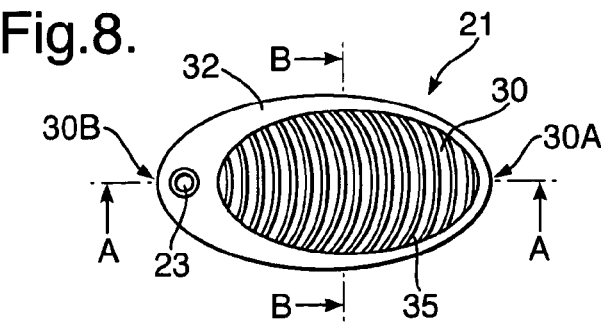
FIG. 8 shows a plan view of another tongue cleaning surface.
Figure 9:
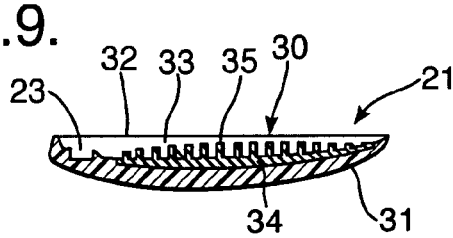
FIG. 9 shows a sectional view of the tongue cleaning surface of FIG. 8 cut in the longitudinal direction.
Figure 10:
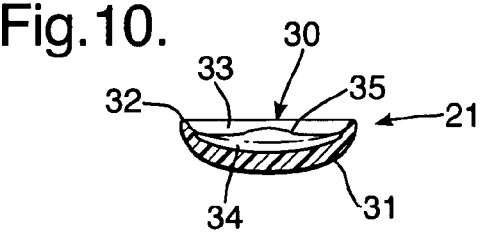
FIG. 10 shows a sectional view of the tongue cleaning surface of FIG. 8 cut across the longitudinal direction.

FIGS. 8, 9 and 10 show further detail of a preferred form of first part 21 with a tongue cleaning surface 30 suitable for use as the tongue cleaning surface of the device shown in FIGS. 1 to 7. Feature 23 indicates a female socket suitable for a male plug to snap fit into to provide a pivot connection to a second part 22. The tongue cleaning surface 30 has a forward end 30A and an opposite rear end 30B. The part 21 comprises a shell 31 made of a plastics material, defining the upper rim 32 of a concavity 33, and is overall of an oval shape as seen in plan in FIG. 8 with its long axis A-A extending longitudinally in the tongue cleaning direction. The lower surface of concavity 33 is provided by an elastomeric member 34 located on the interior surface of the shell 31. The concavity 33 has depth direction being the upward direction as seen in FIGS. 9 and 10 and the direction of the plan view FIG. 8 perpendicular to the longitudinal tongue cleaning direction A-A. The upper surface of member 34 is integrally made into plural ridges 35 having a ridge length direction, viz. the vertical direction as seen in FIG. 8 transverse to the tongue cleaning direction A-A. Ridges 35 are arranged sequentially longitudinally in the tongue cleaning direction A-A. As is seen in FIG. 10 each ridge 35 has a profile in the ridge length direction which rises away from the bottom surface of the concavity 33, i.e. the upper surface of member 34, in a convex curved shape which comprises a curved convex peak with a curved concave dip on either lateral side of the peak. The height to which the curved convex shape of the profile of each ridge 35 rises above the bottom surface of the concavity 33 is less than the depth of the concavity in the vicinity of the ridge 35. This has the consequence that, as can be seen in FIG. 10, the edge of the ridge 35 remote from the bottom surface of the concavity 33 lies below the upper rim 32 of the concavity 33.

As seen in FIG. 8 the ridges 35 have their ridge length direction gently curved, in an arc which is convex in the direction in which the member is to be inserted into the user's mouth.

As is seen in FIG. 9 the edges of plural ridges 35 all lie in a convex curve as seen in the section in the tongue cleaning direction. As also seen in FIG. 9 the edges of the plural ridges 35 all lie in a line which descends in the height direction of the ridges 35 as sectioned along the longitudinal tongue cleaning direction A-A from the forward end 30A toward the rear end 30B, the width direction being designated B-B.

Figure 11:
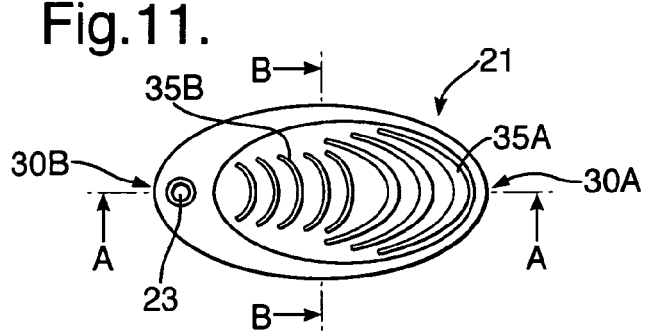
FIG. 11 shows a plan view of another tongue cleaning surface.
Figure 12:
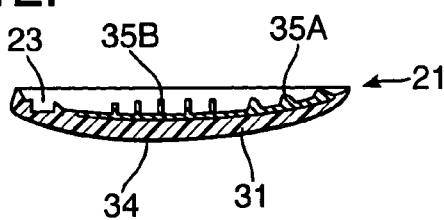
FIG. 12 shows a sectional view of the tongue cleaning surface of FIG. 11 cut in the longitudinal direction.
Figure 13:
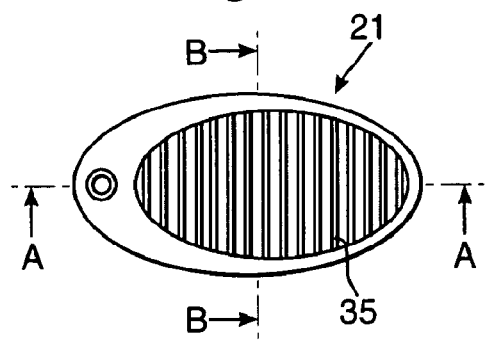
FIG. 13 shows a plan view of another tongue cleaning surface.

FIGS. 11 and 12 show a construction of the part 21 analogous to FIGS. 8 and 9, in which less flexible ridges 35A are located nearer to the forward end 30A. and more flexible ridges 35B are located nearer to the rear end 30B. The less flexible ridges 35A have a greater thickness in the tongue cleaning direction than more flexible ridges 35B, and have a lesser height:maximum thickness ratio relative to the more flexible ridges 35A. In FIGS. 11, 12 and 13 the ridges 35 also have a cross section when cut along the tongue cleaning direction A-A which is asymmetrical as cut along this direction, in that the end radius of the ridge 35 closer to the rear end 30A is greater than the end radius of the ridge adjacent to the 'front end 30B.

FIG. 13 shows a construction of the part 21 analogous to FIG. 8 in which ridges 35 are arranged with their ridge length direction is a straight line perpendicular to the longitudinal direction A-A.

Figure 14:
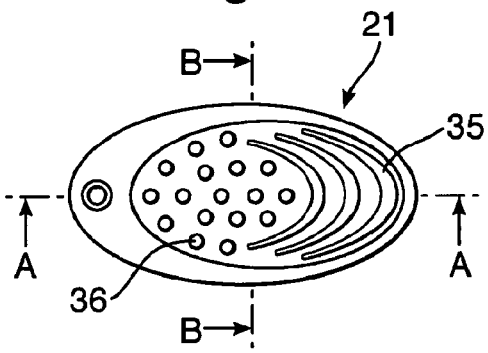
FIG. 14 shows a plan view of another tongue cleaning surface.
Figure 15:
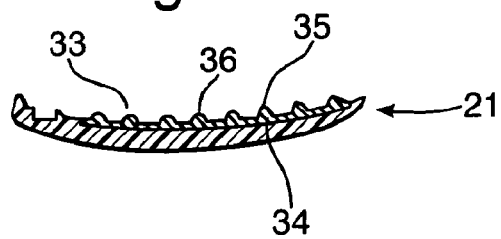
FIG. 15 shows a sectional view of the tongue cleaning surface of FIG. 14 cut in the longitudinal direction.

FIG. 14 shows a plan view of a part 21 analogous to FIG. 8 in which ridges 35 are combined with tongue cleaning means being domed or conical integral projections 36 from the tongue cleaning surface, i.e. from the upper surface of member 34. The projections 36 are located on the surface 34 closer to the rear end 30B. FIG. 15 shows a longitudinal sectional view of the device of FIG. 14 corresponding to FIG. 9.

In the devices of FIGS. 11-15 the ridges 35 have a profile as cut longitudinally. analogous to that of FIG. 10.

Figure 16:
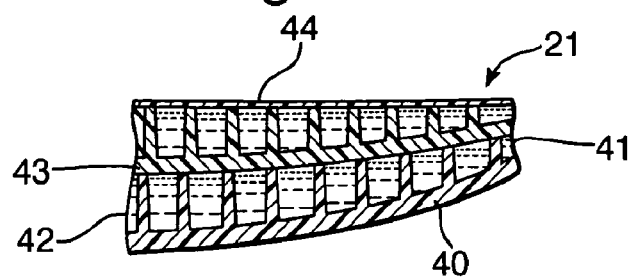
FIG. 16 shows detail of construction of a device of this invention.

FIG. 16 shows detail of part of a further construction of a part 21 particularly for the part 21 of FIGS. 8 to 15, and parts corresponding to FIGS. 8 to 15 are numbered correspondingly. The part 21 comprises a shell 40 made of a plastics material, defining the bottom surface of a cavity 41, and from which plural ribs 42 extend upward into the cavity 41. The plural ribs 42 are made integrally with the plastics material shell 40 and, their rib length direction extends across the longitudinal direction i.e. into the plane of the drawing. An elastomeric member 43 is supported on the surface defined by the upper edges of the plural ribs 42 and has plural ridges 44 analogous to the ridges 35, integrally formed on its upper surface.

Referring to FIG. 17 a device of the invention 50 is shown schematically comprising a first part 51 and a second part 52, pivotally connected at 53, analogous to FIGS. 5, 6 and 7 above. Part 51 incorporates a tongue cleaning surface 54 analogous to that of FIGS. 5, 6 and 7, and part 52 incorporates a surface 55 which covers the tongue cleaning surface 54 when the device 50 is in its second position as shown in FIG. 17. The second part 52 incorporates plural apertures 56 therein providing communication of air between the outside of the device 50 and the tongue cleaning surface 54.

Referring to FIG. 18 various means are shown whereby a device 60 of two-part construction analogous to FIGS. 5, 6, 7 and 17 may be placed in a rest position in which the tongue cleaning surface is aligned with a vertical component so that residual liquid on the tongue cleaning surface will tend to run off FIG. 18A shows a device 60 with a second part 61 shaped with a flat base 62 upon which the device may be stood such that the tongue cleaning surface 63 is aligned inclined at an angle greater that 45° to the horizontal. FIG. 18B shows a device 60 where a base 64 is provided by the profile of the outer surface of a reservoir 65 incorporated into the device 60 and projecting beyond the envelope of the device, and on which the device 60 may stand with its tongue cleaning surface 66 aligned vertically. FIG. 18C shows a device provided with a support 67 hinged to the second part at 68, which may hinge outwardly as shown to support the device 60, in the manner of a support leg, with its tongue cleaning surface 69 in such an alignment. The support 67 may hinge back flush against the outer surface of the device 60 and lock into such a flush position with for example a snap-fit interlock with the device 60. FIG. 18D shows a device 60 of two part construction analogous to FIGS. 5, 6, 7 and 17, provided together with a cradle 610 in which it may rest and which supports the device 60 with its tongue cleaning surface 611 in such an alignment. The devices 60 shown in FIG. 18 are preferably provided with drain holes (not shown) to allow excess fluid to drain out, additionally or alternatively the junction between the first and second parts may be sufficiently non-watertight that fluid drains out via this junction.

Referring to FIG. 19 a construction of device 70 is shown in which the first 71 and second 72 parts are relatively pivotally moveable in a "clamshell" configuration. The first part 71 including the tongue cleaning surface 73 and the second part are hinged by hinge 74 adjacent their respective perimeters. As seen in FIG. 19B the second part 72 is able to swing through ca. 180° in a swing plane perpendicular to the plane of the tongue cleaning surface 73, about a pivot axis A-A seen in FIG. 19C generally parallel to the plane of the tongue cleaning surface 73. The device 70 has a pump operating button 75, from which tongue cleaning fluid may be dispensed from orifice 76.

Referring to FIG. 20 a device 80 is shown in which the first 81 and second 82 parts are completely separable from each other to thereby expose the tongue cleaning surface 83. Parts 81, 82 are releasably connected together by means of the small snap-fit connections 84 arranged about their respective perimeters. FIG. 20A shows the parts 81, 82 in their connected together configuration, and FIG. 20B shows them separated for use. The device 80 has a pump operating button 85, from which tongue cleaning fluid may be dispensed from orifice 86.

The invention claimed is:

1. A device configured for tongue cleaning comprising;
   a tongue cleaning surface comprising a surface of an elastomeric member which is supported for tongue cleaning by running the surface across and in contact with the tongue in a tongue cleaning direction,
   a reservoir for a tongue cleaning fluid,
   means to dispense said fluid either (a) onto the tongue cleaning surface, or (b) directly onto the user's tongue,
   a cover part,
   wherein the tongue cleaning surface and cover part are relatively moveable between a first position in which the tongue cleaning surface is exposed for use and a second position in which the tongue cleaning surface is covered by the cover part wherein the tongue cleaning surface comprises a member defining a concavity having a bottom surface and bounded by an upper rim and having a depth direction perpendicular to the tongue cleaning direction, and supported within the concavity at least one ridge adapted to contact the surface of the user's tongue, the at least one ridge having a ridge length direction transverse to the tongue cleaning direction, a ridge thickness in the tongue cleaning direction, and a ridge height perpendicular to the tongue cleaning direction, wherein the at least one ridge has a profile in the ridge length direction which rises away from the bottom surface in a convex curved shape with its highest point adjacent the transverse mid point of the concavity and with a curved concave dip on either lateral side of the highest point, and wherein the height to which the curved convex shape of the profile of the ridge rises above the bottom surface of the concavity is less than the depth of the concavity between the upper rim and the bottom surface in the vicinity of the ridge, the device being constructed in two parts being a first part comprising the tongue cleaning surface, and a second part comprising the cover part, and the first and second parts are relatively moveable so that in the second position the cover part covers the tongue cleaning surface, the tongue cleaning surface and the cover part both comprise surfaces which in the second position are in a facing relationship with each other and in close proximity, the first and second parts being pivotally movable relative to each other so that in the second position the cover part covers the tongue cleaning surface by means of a pivotal connector that allows such pivoting movement, the second part incorporating a reservoir of the tongue cleaning fluid, with a pump means to pump the fluid from the reservoir to a dispensing orifice from which the fluid may be dispensed, and a conduit to convey fluid from said reservoir in said second part to said tongue cleaning surface passing through said pivotal connector.

2. A device according to claim 1 characterised in that in its ridge length direction the at least one ridge is a straight line, or is curved in an arc which is convex in the direction in which the member is to be inserted into the user's mouth.

3. A device according to claim 1 characterised by plural ridges arranged sequentially in the tongue cleaning direction.

4. A device according to claim 3 characterised in that the edges of plural ridges lie in a convex or concave curve as sectioned in the tongue cleaning direction such that in use the ends in such convex or convex curve contact the user's tongue.

5. A device according to claim 3 characterised in that the edges of plural ridges lie in a line which as sectioned along the tongue cleaning direction from the forward end toward the rear end descends in the height direction of the ridges.

6. A device according to claim 3 characterised by plural ridges arranged sequentially in the tongue cleaning direction in which less flexible ridges are concentrated nearer to or adjacent the forward end of the tongue cleaning surface, and more flexible ridges are concentrated nearer to or adjacent the rear end.

7. A device according to claim 1 characterised in that a ridge has a cross section when cut along the tongue cleaning direction which is an asymmetrical section in that the end radius of the ridge adjacent to the direction in the tongue cleaning direction in which the ridge is to be inserted into the user's mouth is greater than the end radius of the ridge adjacent to the direction in the tongue cleaning direction in which the ridge is to be removed from the user's mouth.

8. A device according to claim 1 characterised in that one or more ridge is combined in the tongue cleaning surface with domed or conical integral projections from the tongue cleaning surface.

9. A device according to claim 1 characterised by an elastomeric member supported by a backing which comprises a part in the form of a shell defining the bottom surface of a cavity, with one or more support extending upward into the cavity, the one or more support supporting the elastomeric member.

10. A device according to claim 1 characterised in that the means to dispense a fluid onto the tongue cleaning surface comprises one or more orifice in the tongue cleaning surface.

11. A device according to claim 1 characterised by one or more aperture therein providing communication of air between the outside of the device and the tongue cleaning surface when the cover part is in its second position.

12. A device according to claim 1 characterised by a base upon which it may be stood such that the tongue cleaning surface is aligned at an angle of 45° or more to the horizontal so that residual liquid on the tongue cleaning surface will tend to run off.

13. A device according to claim 1 characterised by a support which may support the device with the tongue cleaning surface aligned at an angle of 45° or more so that residual liquid on the tongue cleaning surface will tend to run off.

14. A device according to claim 1 characterised by being provided together with a cradle in which it may rest and which supports the device with the tongue cleaning surface aligned at an angle of 45° or more so that residual liquid on the tongue cleaning surface will tend to run off.

* * * * *

UNITED STATES PATENT AND TRADEMARK OFFICE
CERTIFICATE OF CORRECTION

PATENT NO. : 8,088,133 B2
APPLICATION NO. : 11/912426
DATED : January 3, 2012
INVENTOR(S) : Mary Lynn Bosma et al.

It is certified that error appears in the above-identified patent and that said Letters Patent is hereby corrected as shown below:

On the Title page, Item [22]

"(22) PCT Filed: Apr. 21, 2005" should read as -- (22) PCT Filed: Apr. 21, 2006 --

Signed and Sealed this
Sixteenth Day of April, 2013

Teresa Stanek Rea
*Acting Director of the United States Patent and Trademark Office*